United States Patent
Brevnova et al.

(10) Patent No.: US 8,099,297 B2
(45) Date of Patent: Jan. 17, 2012

(54) BUSINESS METHOD AND SYSTEM FOR ORDERING, PURCHASING AND STORING STEM CELLS

(75) Inventors: Elena Brevnova, Lebanon, NH (US); James Justin Lancaster, Quechee, VT (US)

(73) Assignee: Hydrojoule, LLC, Lebanon, NH (US)

( * ) Notice: Subject to any disclaimer, the term of this patent is extended or adjusted under 35 U.S.C. 154(b) by 679 days.

(21) Appl. No.: 12/009,793

(22) Filed: Jan. 22, 2008

(65) Prior Publication Data

US 2008/0215364 A1    Sep. 4, 2008

Related U.S. Application Data

(60) Provisional application No. 60/881,638, filed on Jan. 22, 2007.

(51) Int. Cl.
*G06Q 10/00* (2006.01)
*G06Q 50/00* (2006.01)

(52) U.S. Cl. .......... 705/2; 705/3; 705/330; 600/300
(58) Field of Classification Search .......... 705/2–3, 705/10, 26, 330; 600/300
See application file for complete search history.

(56) References Cited

U.S. PATENT DOCUMENTS

| | | | |
|---|---|---|---|
| 2004/0267562 A1 | 12/2004 | Fuhrer et al. | |
| 2005/0158864 A1* | 7/2005 | Brant et al. | 436/37 |
| 2005/0233298 A1* | 10/2005 | Farsedakis | 435/1.1 |
| 2005/0266494 A1 | 12/2005 | Hodge | |
| 2008/0033758 A1* | 2/2008 | Keeley | 705/2 |
| 2009/0192854 A1* | 7/2009 | Pietrucha et al. | 705/7 |

OTHER PUBLICATIONS

Cryo-Cell Announces Corporate News to Be Disseminated at Jun. 20th Shareholder's Meeting, Jun. 20, 2000, PR Newswire, page 1.*
Li; Morphology Study of Freeze-Drying Mononuclear Cells of human cord blood; CryoLetters; 2005; pp. 193-200; 26 (3); London, UK [pp. 193-196 describe a process to freeze-dry cord blood; however, no mention of storage methods or containers beyond word "vials" and no mention of associated business method for delivering services between customers and medical facilities].
Xiao; Freeze-drying of mononuclear cells and whole blood of human cord blood; CryoLetters; 2004; pp. 11-120; 25 (20); London, UK [p. 112-115, mentioning advantages of storing at room temperature and describing a process to freeze-dry cord blood].
Myers; Dry storage of sperm: applications in primates and domestic animals; Reprod Fertil Dev. (CSIRO Publ.); 2006; pp. 1-5; 18 (1-2); Colingwood, Victoria, Australia [p. 1, mentions lyopreserved stem cells can provide long-term storage without need for expensive and burdensome cryogenic conditions, and gives methods for freeze-drying biological material].

* cited by examiner

*Primary Examiner* — Luke Gilligan
(74) *Attorney, Agent, or Firm* — J. Justin Lancaster

(57) ABSTRACT

An online business method and system enables donors or parents or guardians of donors to order and purchase stem-cells from biological tissue sampled from the donor, such as, for example, cord-blood stem cells of a newborn baby, wherein the ordering process interfaces directly with the attending medical services, and the service steps include collection, extraction, preservation, containment, packaging, delivery and storage of the stem cells in a storage medium that can be cost-effectively maintained by the donor, parent or guardian at home or in a custodial location. In one embodiment, preservation is by freeze-drying, containment is in a vacuum vial, and storage is at room temperature.

70 Claims, 8 Drawing Sheets

BUSINESS METHOD AND SYSTEM FOR ORDERING, PURCHASING AND STORING STEM CELLS

RELATED APPLICATION

This application claims priority to Provisional Patent Application No. 60/881,638, filed Jan. 22, 2007, the entire teachings of which are incorporated herein by reference.

FEDERALLY SPONSORED RESEARCH

N/A

BACKGROUND

Haematopoietic stem cells of human umbilical-cord blood have become more important recently, for it is recognized that such cells have potential biomedical uses in the potential treatment of the many diseases. Such stem cells are particularly valuable to the individual from whom they were extracted, for they can have a greater probability of being recognized as familiar (i.e., not foreign, or antigen) by the immune system, thus potentially avoiding auto-immune response to those cell's, or to other cells or biological material grown from those cells.

Typically, cord blood is preserved at ultra-low temperatures, which are expensive to produce and maintain, and which require special, low-temperature storage facilities. Cryopreservation and storage currently require liquid nitrogen or ultra-low-refrigeration-based methods for long- or short-term storage, which requires routine maintenance and extensive space requirements. The preservation of stem cells also has strict requirements for long-term storage to maintain genetic integrity. Therefore, individuals, such as parents who want to store stem cells of their newborn children, are presently required to utilize an elaborate cryostorage facility, at substantial cost to themselves and with reduced personal control over the biological material of their family and child. Typically, parents must pay an initial processing fee and then continue to pay into the future an annual storage fee. There is also substantial uncertainty that a cryostorage company will remain a viable business entity for many decades, or that said company will not lose the stored specimens. The potential for such business failures or mistakes increases the risk insurance that such a business entity must carry, with the insurance cost being passed on to the end-user customer.

It is desirable, then, to have a method for enabling donors generally, and parents and/or guardians of newborns in particular, to obtain, possess and keep control over a stored donor sample, or specimen cells (e.g., stem cells from the umbilical cord blood of a newborn child), which sample or specimen cells, with some degree of probability, can be resuscitated later by medical professionals at the direction of the parent and/or the donor himself or herself in the event that such cells are later needed for a medical procedure. Further, it is desirable to make this method available to parents through a straightforward and economically feasible service that is reasonably approachable as part of a normal child-birth experience. It is a further goal to reduce or eliminate ongoing annual storage costs by avoiding continuing cryostorage. It is a further goal to provide a business method and system that employs computerized, automated steps and standardization at numerous points in the process in order to further improve handling-efficiencies and thereby increase cost savings owing to these efficiencies and reduction of human labor costs. It is a further goal to reduce business cost and customer cost by developing a business method and system that can, by transferring possession and responsibility for long-term storage to the customer or to a greater variety of $3^{rd}$ party custodians who may be chosen by the customer, reduce potential and real legal and insurance costs that would otherwise burden the stem-cell preservation and storage provider-service business

SUMMARY

Preferred embodiments of the invention provide generally for a business method and system that enables parents or guardians of soon-to-be-born or newborn babies to request and purchase the haematopoietic stem cells of the cord blood of their newborn baby through an Internet-based service, wherein the service business further provides a substantially simplified ordering process and steps, which process and steps can optionally interface directly and/or automatically with those primary attending physician(s) and/or medical clinicians attending, assisting and/or supervising the birth of the newborn child, and which processes and/or steps include the completing of collection, extraction, preservation, containment, packaging delivery and storage of the stem cells in a storage medium that can be cost-effectively maintained by the parent, guardian and/or representative at any location they may choose, including, for example, without limitation, in their own home or with a custodian and in a custodial environment of their choosing (such as, for example, in a commercially maintained safe-deposit box). Further, preferred embodiments provide for the stem cells to be delivered in straightforward fashion to the parents and or guardians, or their representatives, in a storage mode that is inexpensive and simple to maintain with the samples in full possession and control of the parents, guardians or representatives (one such storage mode being, for example, a freeze-dried preservation and storage method allowing storage in a protective container (such as, for example, a vacuum ampule) and at temperatures above zero degrees Centigrade.

A further preferred embodiment of the invention provides for a specifically designed vacuum ampule that is provided with the storage service that can hold freeze-dried stem cells, at least at room temperature, out of contact with oxygen or other degrading gases or chemicals for a substantial period of days-to-years. A further embodiment provides for such an ampule wherein integral to the ampule is maintained an optional set of at least one aspect of key medical information about a newborn baby's identity, medical history, legal information, details of the sample preservation and/or a recommended rejuvenation procedure for the stored cells. Embodiments of the invention can provide for this information to be stored in association with the sample, attached to the sample, or integral in or within the sample container itself. Preferred embodiments can include magnetic information storage, optical information storage, and/or microdot photographic storage.

A further embodiment provides for a storage service that includes one or more of the following steps and/or processes: a Web-based ordering page; the web-ordering page connected automatically to a secondary, automated service-order directive transmission; the order and purchase process connected to an optionally clinician-supervised step of automatically preserving and storing the stem cells; the order and purchase process connected to a step of delivering the storage vial (or ampule) to a secure storage location maintained by a 3rd-party provider (such as, for example, a safe-deposit storage box in a bank or other facility); the purchase process connected to a step of delivering to the purchaser a physical key to the storage facility and lock-box or a "delivery key code" that enables the purchaser at any chosen time to initiate physical delivery of the stored vial to the purchaser's possession.

While preferred embodiments are described that pertain to newborn babies and umbilical cord blood, other embodiments can provide for a business method for selling storage services and/or a storable stem-cell product for a variety of potential customers and/or patients, including stem cells derived from blood and/or other tissues of adults, wherein certain preservation methods allow storage of the stem cells in a protected environment at non-refrigerated temperatures, such as at above zero degrees Centigrade, at ambient temperatures, and/or preferably at about room temperature, and wherein the method of selling includes automatically creating the service order for the medical sampling and preservation procedure based on a customer's online order and, further, wherein delivery of the sample to the customer and/or to a storage facility is assisted in the business process by a preaddressed and coded mailing envelope provided as part of the business service and automatically labeled and addressed as part of the step of providing the service order to the medical practitioners.

A further preferred embodiment of the business method includes the steps of providing for a transmittal envelope that is especially suited and/or designed for a particular storage container and routing to a particular storage facility, whereby the transmittal envelopes bear sufficient identifying coding so that the envelopes can be automatically manipulated by robotic handling, processed, stored and later retrieved and reshipped based on the exterior coding.

A preferred embodiment of the business method provides additional steps and procedures for closing the dry-stored stem cells in a vacuum ampule. The vacuum ampule can be created by a "flame-off" process that seals a glass pipette on a vacuum rack, the pipette having been previously loaded with freeze-dried specimen cells. Alternatively, the storage container can be glass, plastic or metal. A primary storage container can be secondarily contained or enclosed in a secondary storage container. The primary container, secondary container or both containers can be transmitted in a special envelope designed to enclose the containers and to carry descriptive, coded information on the exterior of the envelope, which envelope can be transmitted by U.S. Postal Service or by private courier. The special envelope, or special mailing containers, can additionally be specially designed for automated processing by robotic handling, as well as for automated storage in storage carousels managed by automatic handling equipment (or robotics).

A further embodiment provides for transmitting the container with storage directions and/or with usage directions. The storage directions and/or usage directions can be combined with other data incorporated into a data component that is affixed to or otherwise permanently integrated with the primary container, secondary container and/or special envelope or special mailing container.

A preferred embodiment of the business method provides for storing the stem cells in a dried form (dry-storing), which includes a freeze-drying step in the processing and preservation of the extracted cells.

A preferred embodiment of the business method provides additionally for offering and selling the service as a prepaid component of an obstetrical service.

A preferred embodiment of the invention provides for a stem-cell-storage, service-business system comprising: a database that stores information about a plurality of medical service professionals, hospitals, clinics or a combination thereof who deliver at least one of the services of delivering babies, attending births, taking samples of umbilical cord tissue or blood, storing umbilical cord tissue or blood, extracting cord blood stem cells, and storing cord blood stem cells; business system software; an application server that is connected to the database and accessible to customers via an Internet connection and that hosts the business system software; a communication means that communicates information about the professional, hospitals, clinics or a combination thereof to potential customers of the business system, communicates information about one or more customers' choosing of services of the professionals, hospitals, clinics or combination thereof to the business system, or both; an input means, whereby a customer inputs information to a relational database relative to the customer; and a planning means that plans stem-cell storage for a customer accessing the system, wherein said information in said database is stored in a form of a relational database, wherein a customer accessing the application server through an Internet connection causes the business system software to initiate the planning means based on input information from the customer, wherein the planning means connects or relates the customer's input information to information about the medical services and retrieves from the relational database information sufficient to complete and deliver a standard service order.

Another preferred embodiment provides a computer implemented system for selling stem cell storage services comprising: a database containing storage-method and medical-service-provider information wherein the storage-method and medical-service-provider information comprises service provider data and pre-storage processing and storage methods; an online purchasing interface where a customer or a reseller accesses the purchasing interface to acquire at least one storage service; a planning interface where a customer accesses a presentation of available options for medical services to acquire at least one storage-service product; a front office interface for providing purchase order information and marketing information and for receiving at least one order from at least one customer wherein the at least one order is related to at least one of the plurality of stem cell storage service products; and a processor for processing orders received from the front office interface; wherein the database, the purchasing interface, the planning interface, the front office interface, and the processor are interoperably connected.

A further embodiment of the invention provides a method for selling the service of storing stem cells of a donor and re-infusing these cells into the donor when older, comprising: selling a prepaid stem-cell storage service to a donor or a guardian or relative of the donor; harvesting a biological specimen containing stem cells from the body of the donor; storing at least a part of said biological specimen that contains stem cells for a predetermined period time without being re-infused into the donor; and reintroducing at least a portion of said stored part of the biological specimen containing stem cells in therapeutic amount in the donor after the predetermined period of time and after said donor is diagnosed with an illness or a damaged tissue of the donor is in need of rejuvenation, wherein said re-introduced specimen is revived from a freeze-dried state prior to re-infusion. The method can include effectively storing the stem cells at ambient temperature or at about room temperature, or at unrefrigerated temperatures, or effectively storing the stem cells over the range of about 18-25 degrees Centigrade (C). A further embodiment can provide for the donor to be a newborn child and effectively storing the stem cells at least over a period of more than 2 years at an average storage temperature of more than 0 degrees Centigrade (C) and with a less than a 10% loss in the number of stem cells that are able to be resuscitated owing to the term and method of storage.

Another preferred embodiment provides a business method comprising: establishing a stem cell storage plan for a selected customer wherein the stem cells are stored at an average temperature of greater than 0 degrees C.; collecting a fee from the customer to effect and maintain stem cell storage; paying a service company a predetermined fee in support of services performed by said company on behalf of said customer; and accounting for said fee from at least one of said customers. The services can continue over an indefinite period of time and said fee can be a single prepaid fee. A portion of all services provided by the service company or companies on behalf of the customer can include other services, including initialization services, and the other services can also include, without limitation, paying the service company or companies for performance of the initialization services. The services can include storage and preservation of biological materials and said initialization services can include collection, testing and processing services. The biological materials can be stem cells, umbilical cord blood, placental blood, DNA, peripheral blood, bone marrow or other materials, and these materials can belong to a member of the customer's family. The services can include services to be provided for a third-party beneficiary named by the customer, with the company storing biological materials belonging to a member of said beneficiary's family, including biological materials of the beneficiary himself or herself. This can include receiving from the customer notice or notification that identifies the beneficiary (such as, for example, a soon-to-be-born child), and can further include forwarding an identification of the beneficiary to the company providing the services. Embodiments can provide for receiving notice that services performed by said company on behalf of said customer have changed and, after receiving of the notice, adjusting said fee paid to said company. Also the change in the services provided by the company can include the termination of services on behalf of the customer, and adjusting the fee can include adjusting the fee to zero and terminating payments made to the company.

A further preferred embodiment provides a business method for selling stem-cell storage comprising: establishing a stem-cell storage contract for a selected customer; collecting a prepaid fee at to effect said storage; establishing a value for said storage contract; periodically paying a storage services company a fee in support of storage services performed by said storage services company on behalf of said customer; and accounting for said fee from at least one of said fee and said value. A further method can provide for selling a storable, stem-cell product or storage service to a customer, comprising the steps of: providing an offer to at least one potential customer to sell a service of storing stem cells or to sell a storable stem cell product; registering a customer order responsive to the offer; extracting blood or tissue from the customer, in keeping with the customer order to produce a blood or tissue sample; dry-storing stem cells from the blood or tissue sample; closing the dry-stored stem cells in a container; and storing the container. The container can be preferably stored at above zero degrees Centigrade, delivered after closing to the customer, with the customer storing the container.

BRIEF DESCRIPTION OF THE FIGURES

Other features and advantages of the invention will be apparent from the following description of the preferred embodiments thereof and from the claims, taken in conjunction with the accompanying drawings, in which:

DETAILED DESCRIPTION

Figure 1:
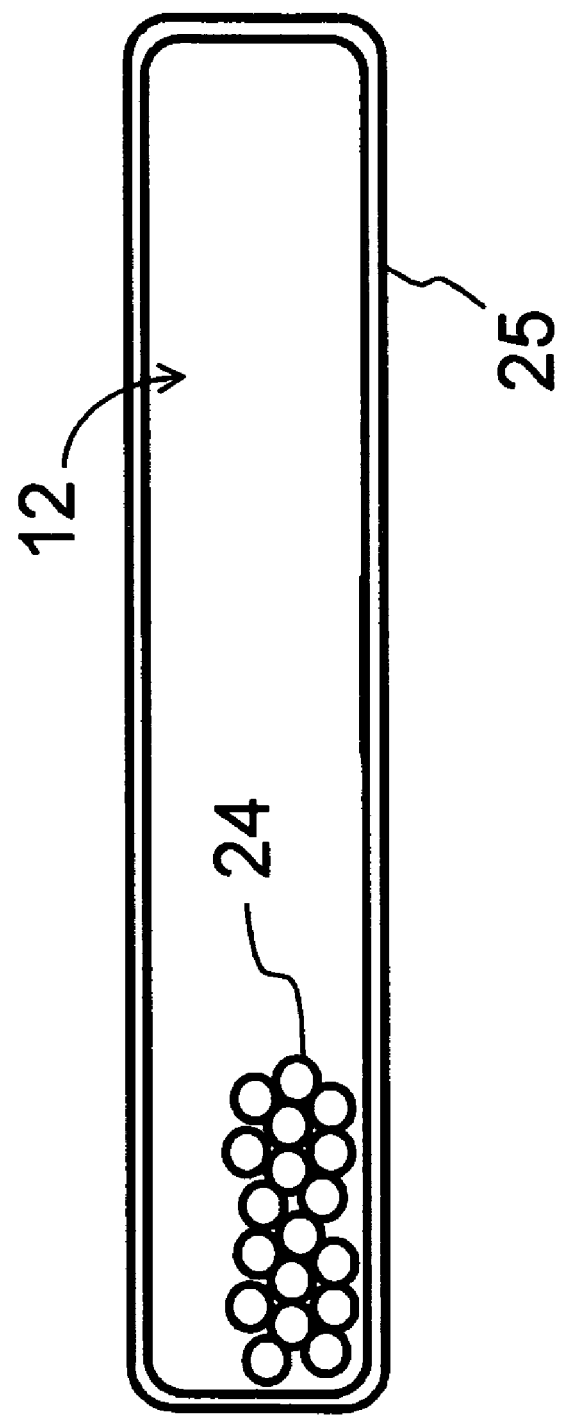
FIG. 1 illustrates a stem-cell storage container according to an embodiment of the invention.

A preferred embodiment of the invention provides for a parent and/or guardian of a soon-to-be born child to order, schedule and/or purchase the service of sampling, preserving and storing their child's stem cells in a manner that allows the parent easy long-term storage and control over the sample.

The method and system of the invention are additionally described in U.S. Provisional Patent Application No. 60/881, 638, filed Jan. 22, 2007, which is incorporated herein by reference in its entirety.

A preferred embodiment provides a method for selling a storable, newborn-stem-cell product or storage service to parents or guardians of newborn children, comprising the steps of providing an offer to at least one potential customer to sell a service of storing stem cells (or to sell a storable stem cell product), registering a customer order responsive to the offer, generating a service order based on the customer order, extracting blood from the umbilical cord of a newborn baby, according to the service order to produce a cord-blood sample, dry-storing stem cells from the cord-blood sample, closing the dry-stored stem cells in a container and storing the container. Preferably, the blood is extracted from the umbilical cord within 72 hours of birth. The dry-stored stem cells are preferably closed in a container with an airtight seal and the method of preservation and containment provides effective storage at about room temperature. After closing the stem cells in a container, the container can be transmitted to a parent or a guardian of the newborn baby or to a representative of said parent or guardian.

A further preferred embodiment of the invention provides a system for generating a stem-cell-storage service order, relative to a prospective new-born baby or an adult customer, or both, comprising: a database storing stem-cell-storage service-order information about each of a plurality of medical device service providers; and a computer system communicably coupled to the database, the computer system including computer program instructions to:

(a) provide a first user interface to accept, from a first user, an identification of one of the plurality of medical service providers and information identifying a service provider who is to be authorized to provide the service of stem-cell extraction, preservation, packaging and package delivery, relative to a baby, a customer, or both;

(b) determine if the first user is authorized to enter information into the database;

(c) if the first user is authorized, store information provided by the first user in the database in association with the one of the plurality of medical service providers;

(d) provide a second user interface to accept user credentials and an identification of one of the plurality of medical service providers, wherein the second user interface is accessible by a customer who is not the first user or one of the plurality of medical service providers;

(e) determine if the customer is authorized to generate a stem-cell-storage service-order, relative to the one of the plurality of medical service providers, comprising accessing the database to determine if the user credentials accepted from the customer by the second user interface correspond to information requirements criteria stored in the database in association with the one of the plurality of medical service providers; and (f) if the customer is authorized, generate a service order relating to the one of the plurality of medical service providers and provide the generated service order to the medical service provider.

Ordering and Purchasing Step

Upon signing up for obstetrician's care, or signing up for the hospital birthing services, or by one or more other means at a time prior and/or proximate to the child's birth, a requesting parent can order and purchase the taking of sample, and or further pre-pay for the preservation and long-term storage of the stored stem cells. For instance, FIG. 5 illustrates a sign-up or purchase/order form allowing a parent and guardian of a soon-to-be born child and/or a newborn child to order or schedule the storage service to be conducted and to specify the delivery of the stored product to the purchasing parent and or guardian and/or to the parent or guardian's representative.

The sign-up or purchase form can be on paper, or can be electronic via the Internet and a web service. It is considered within the scope of the invention to provide a web-page presented service for such cord-blood stem cell storage, whereby the service provided arranges directly with the attending physician and/or the birthing clinic or the hospital to provide the desired storage procedure according to the service details selected.

Figure 4:
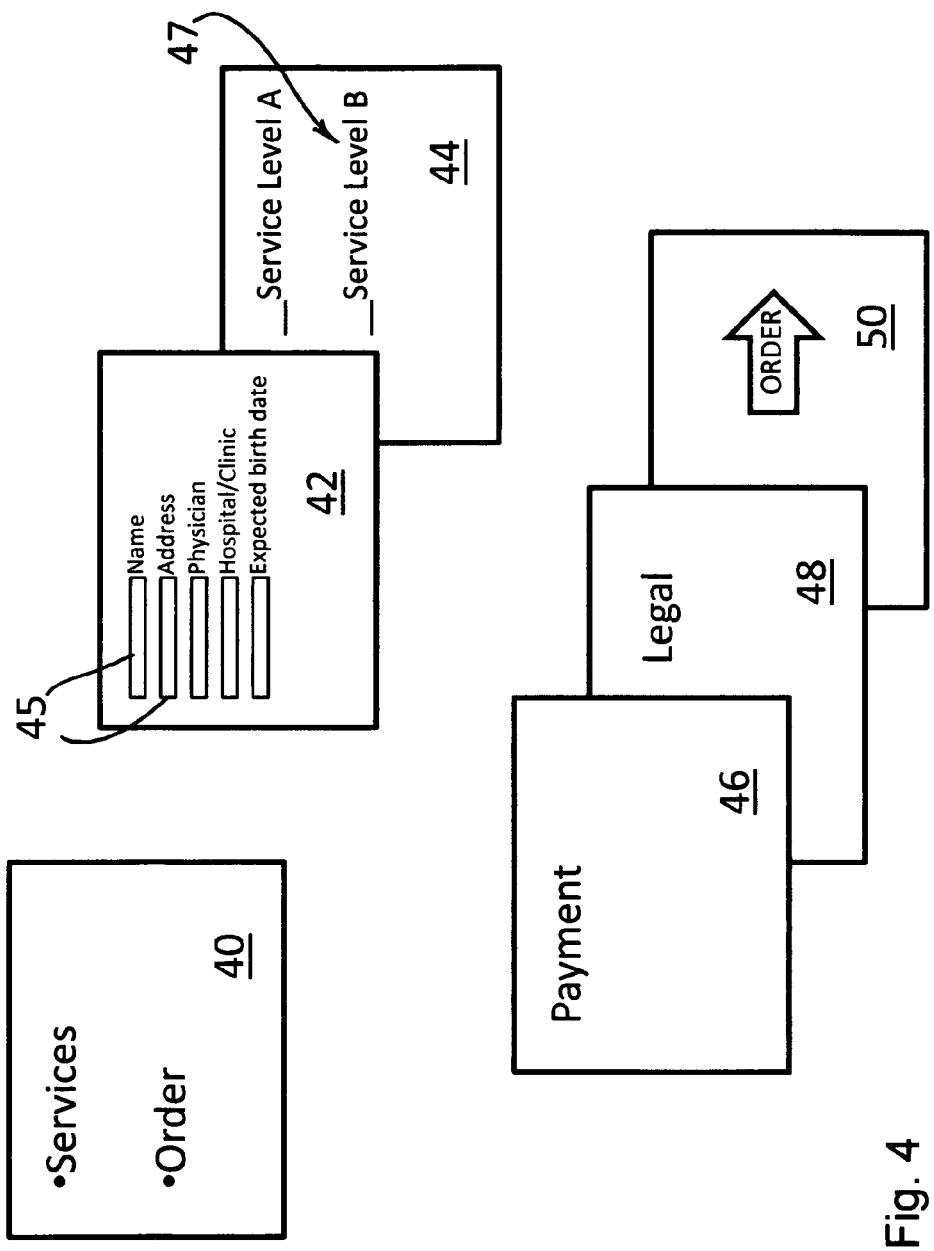
FIG. 4 illustrates a succession of web pages or web screens that can appear according to an embodiment as part of the providing of the offer to the potential customer and the recording of order information and completion of the ordering transaction.
Figure 5:
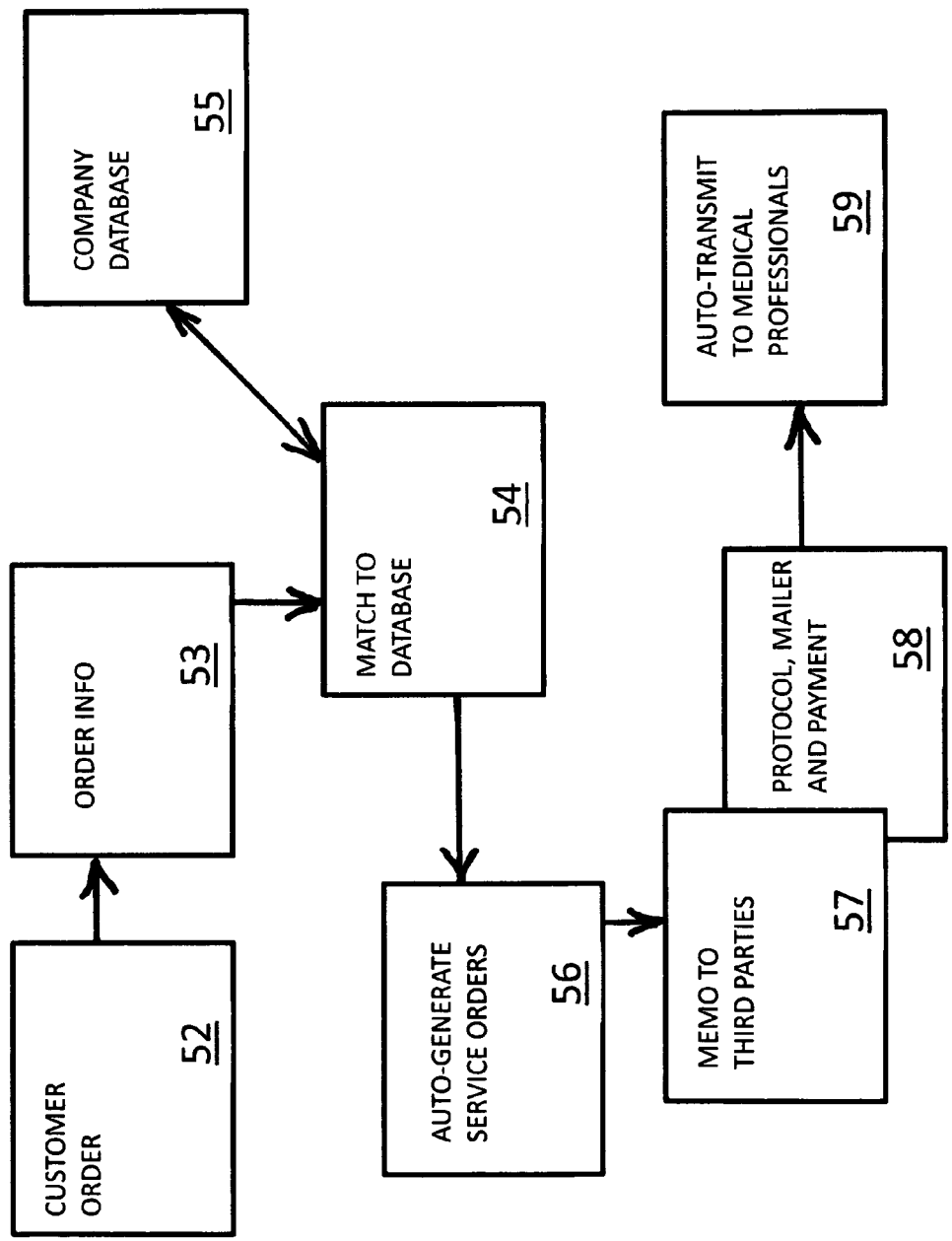
FIG. 5 illustrates business steps according to an embodiment.
Figure 7:
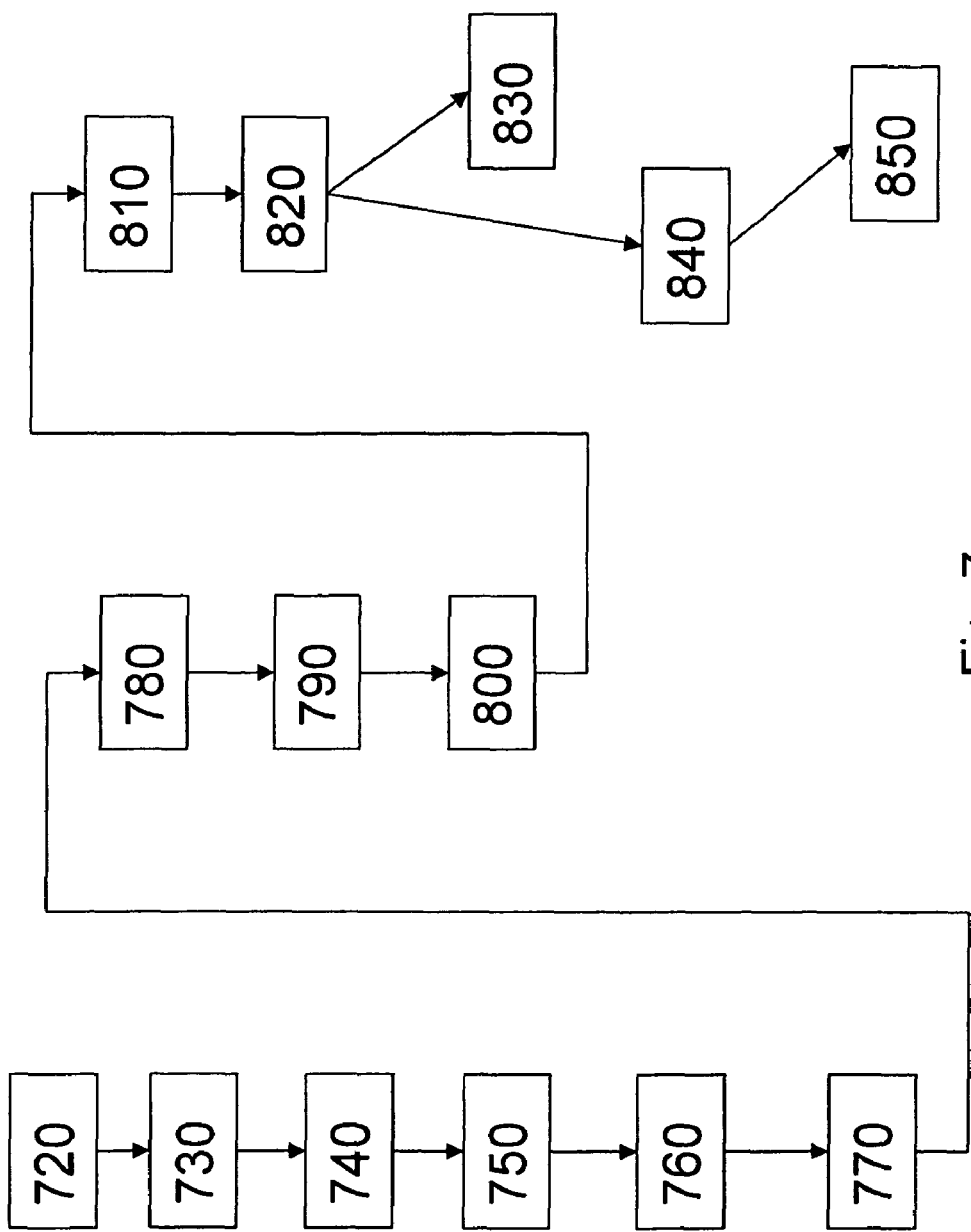
FIG. 7 illustrates a sequence of business steps according to an embodiment of the invention.

FIGS. 4, 5 and 7 illustrate a service presentation and customer sign-up procedure effected over the Internet, with the data being moved to a server and then a secondary order being placed by the service, based on the information in the form, with a forwarded order sheet being delivered by the Internet to participating medical providers, doctors, technicians, clinics and or hospitals. According to known methods, such as, for example, by use of RSA public-key encryption, this ordering service can utilize encryption to keep information confidential.

It is within the scope of the invention to provide further for automated forwarding and/or automated secondary ordering procedures, whereby the parent and or guardian requestor (or a representative of said party) can prepay for the service on a web-page, and the automated service-order is forwarded to the medical professionals and service professionals responsible for attending the birth, and whereby the stored and sealed sample is collected, extracted, preserved, contained, sealed, packaged and posted directly from the birthing clinic and/or hospital, or by the primary attending medical professionals, and delivered to the storage facility or to the customer for long-term storage. Alternatively, an intermediary service step can occur whereby an intermediate team receives cryopreserved blood samples from the hospital and/or medical clinic and/or birthing location and this team performs the preservation and storage-sealing steps and delivers the completed stored samples to the requesting parent and/or guardian, and/or to the representative(s) of same.

Sampling and Preservation Process and Steps

Multiple known methods and steps exist to collect the cord blood from new-born babies at the time of birth. A standard delivery room protocol includes collecting and sending a small sample of umbilical cord blood to the laboratory shortly after delivery of the fetus for a variety of tests. A healthcare professional can insert a needle of a collection bag into the vein of the umbilical cord and withdraw cord blood. Collection takes 5-10 minutes to complete and approximately 1-2 cups of cord blood can be obtained in this manner. Other and sufficient methods for collecting cord blood from a newborn are described in U.S. Pat. No. 6,179,819 to J. N. Haswell.

Recently, the preservation of cord blood stem cells has been achieved at higher temperatures. Experiments on both the mononuclear cell (MNC) content and the whole blood of human cord blood have been carried out successfully. [REFERENCE: Xiao et al., "Freeze-drying of mononuclear cells and whole blood of human cord blood." Cryo Letters. 2004 March-April; 25 (2): 111-20, which is herein incorporated by reference in its entirety]. These known freeze-drying methods can be used to preserve the extracted stem cells according to one embodiment.

Storage Process and Steps

A further preferred embodiment of the invention provides for a specifically designed vacuum ampule that is provided with the storage service that can hold freeze-dried stem cells, at least at ambient or room temperatures, out of contact with oxygen or other degrading gases or chemicals for a substantial period of months to years.

Alternatively, as can be appreciated by one skilled in the art of vacuum storage, the samples can be stored in metal or plastic ampules that have been evacuated after loading with the specimen cells. Alternatively, a further embodiment of the invention provides for storing the sample in a sealed tube from which at least the oxygen has been removed, or from which both the oxygen and the nitrogen have been removed, and those gases may be replaced by an inert gas, such as, for example, helium, neon, argon, krypton, or xenon, inter alia, or the tube can be filled around the sample by a plastic or polymer to otherwise seal the specimen dry-stored mononucleated cells (MNCs) from contact with oxygen.

A further embodiment provides for such a vial or ampule wherein integral to the vial or ampule is maintained an optional set of at least one aspect of key medical information about the newborn baby's identity, medical history, legal information, details of the sample preservation and/or a recommended rejuvenation procedure for the stored cells. Embodiments of the invention can provide for this information to be stored in association with the sample, attached to the sample, or integral in or within the sample container itself. Preferred embodiments can include magnetic information storage, optical information storage, microdot photographic storage.

Following storage of the cells in a sealed container, the container can be delivered to the parent or guardian of the newborn child, or to a representative of the parent or guardian of the child. A "chain of custody," certified by the attending physicians and/or technicians can be attached as a paper document, or on a permanent glass, plastic, metallic or some other material, encoded, encrypted, etc., and this certification can be also placed inside a sealed area of the container. This certification and description of the process and the contents can be also attached in a magnetic fashion, as in an RF-ID tag, bar code, magnetic computer strip or other mode that will allow easy reading with a detector, bar-code reader and/or computing means or automated reader.

A further embodiment provides for a storage service that includes one or more of the following steps and/or processes: a Web-based ordering page; the web-ordering page connected automatically to a secondary, automated service-order directive transmission; the order and purchase process connected to an optionally clinician-supervised step of automatically preserving and storing the stem cells; the order and purchase process connected to a step of delivering the storage vial (or ampule) to a secure storage location maintained by a 3rd party provider (such as, for example, a safe-deposit storage box in a bank or other facility); the purchase process connected to a step of delivering to the purchaser a physical key to the storage facility and lock-box or a "delivery key code" that enables the purchaser at any chosen time to initiate physical delivery of the stored vial to the purchaser's possession.

An embodiment provides for a business method that includes selling services for initiating, collecting, extracting, preserving, containing, packaging, delivering and storing with respect to initiating a process to collect tissues, extract stem cells from those tissues, preserve the stem cells and/or the tissues, contain the stem cells in packaging, deliver the package and/or container to a storage facility or to a customer, and storing the stem cells in the possession of the facility or the customer. An embodiment further provides for effectively storing the stem cells at ambient or at about room temperatures, preferably storing the cells effectively at temperatures within a range of 20-22 degrees Centigrade (degrees C.), preferably within a range of 18-25 degrees C., preferably within a range of 10-37 degrees C., and more preferably effectively storing the stem cells at temperatures higher than zero degrees C. By "effectively storing" it is meant herein that the stem cells can be stored for substantial periods of time, such as, for example more than six months, preferably more than one year, more than five years, more than ten years, more than twenty years and preferably more than forty years, without substantial loss in the number of cells that can be resuscitated, such as, for example, not more than a 50% loss in the number of cells that can be resuscitated, not more than a 30% loss, not more than a 20% loss, and preferably not more than a 10% loss in the number of cells that can be resuscitated. Thus, an embodiment provides for selling stem-cell storage services wherein the loss in number of cells that can be resuscitated is small even when the average storage temperature over a long period of time is relatively high.

An embodiment of the invention provides a business method that provides ordering and purchasing processes and steps for delivering and/or selling to parents of a newborn child a dry-stored sample (specimen) of that newborn baby's stem cells extracted from umbilical cord blood, such that the parents have maximum and flexible control over the sample at a substantially reduced cost. Such an embodiment can be further described by the following example.

Example 1

A preferred embodiment of the business method according to the invention enables a parent of a soon-to-be child to browse to a web-site that offers the service according to the invention. The requesting parent orders the taking of sample, and pre-pays for the preservation and long-term storage of the stem cells in a sealed vial. The requesting parent pays in advance for the service using a bank credit card over the Web. The purchase is fully electronic via the web service, whereby a software module run by the company that is providing this service according to the invention (hereinafter "the Storage Service-Provider Company," or "the SSP Company") on its servers automatically generates (by Active Server Pages, JAVA™ applets, C#, "dot-Net", and/or other similar automated Internet and/or web-based programming technologies known to those skilled in the art of programming) a secondary order page that is directed to the sample storage technicians (who may be employed by the SSP Company or by the hospital or by a 3rd party company) and/or to the primary obstetrical physician attending the mother. The secondary directive document transmits the requestor's authenticated authorization information (identity information that can be verified by the attending physician) and provides specific technical instructions to the attending physician, the hospital and the sample storage technicians. In this example, the storage technicians are employees of the hospital who are certified to conduct the storage procedure and the instructions direct sealing in an evacuated glass vial.

In this example, the automated order has thus been forwarded to the medical professionals attending the birth of the child. The umbilical cord, separated from the child at the time of birth or very shortly thereafter, is sectioned and a blood sample immediately obtained (by standard means, including, but not limited to, pipette suction, vacuum suction, and/or drip collection).

Samples of the blood can be frozen by different cooling protocols in the presence of 40 percent PVP+20 percent sucrose+10 percent Mannitol (fetal bovine serum). Then, the samples can be vacuum-dried at a selected shelf temperature in the range of minus 30 to minus 40 degrees C. for the main drying stage, and then vacuum-dried at 15 degrees C. for the second drying stage (which vacuum drying can preferably be conducted in the range of 1.0 to 0.1 Torr). The entire time of the freeze drying can be in the range of 10 to 100 hours, preferably in the range of 40-80 hours, even more preferably in the range of 50-60 hours, and most preferably can be about 52 hours.

To demonstrate the viability of rejuvenation of the freeze-dried cells, the dried samples can be suspended in an isotonic phosphate-buffered saline solution and then recovery of the cells can be tested by a haemacytometer, wherein viability of the nucleated cells can be measured by PI staining and the ratio of the number of CD34+ to the number of lymphocytes (by the FITC anti-human CD34+ conjugated antibody method) can be measured using a flow cytometer (FCM).

According to the invention, methods for freeze-drying, dry-preserving and dry-storing of the mononuclear specimen cells (MNCs) can include and follow the detailed procedures of Xiao et al., 2004 ["Freeze-drying of mononuclear cells and whole blood of human cord blood." CryoLetters. 2004 March-April; 25(2):111-20], which is hereby incorporated by reference in its entirety, and can include and follow the detailed procedures of Li et al., 2005 ["Morphology Study of Freeze-Drying Mononuclear Cells of human Cord Blood." CryoLetters. 26 (3), 193-200 (2005)], which is also hereby incorporated by reference in its entirety.

The vacuum-dried sample, after the second stage of drying, can be placed in a vacuum ampule. This can be accomplished by pipetting or otherwise transferring a portion of the freeze-dried sample into an open flame-off tube, attaching the flame-off tube to a glass vacuum rack, creating a vacuum in the range of a low vacuum to a medium vacuum (such as, for example, in the range of 700 torr –0.001 torr of evacuation), and then closing the flame-off tube by heat-sealing the glass above the stored sample (a "flame-off tube" as used herein means a thin tube of thin-walled glass—about 0.5 mm to 2 mm thick walls—the tube preferably having an inner diameter in the range of 1 mm to 15 mm, more preferably in the range of 2-6 mm inner diameter and even more preferably in the range of 4-6 mm inner diameter, closed at one end and having an open aperture at the other end that may have a ground-glass flange or similar vacuum-sealable aperture for engaging a stopcock of other valve closure that can enable attachment of the flame-off tube to the vacuum rack, so that by opening the stopcock of other valve means the flame-off tube inner volume is exposed to the vacuum; see FIGS. 2A and 2B, described in more detail below).

The technician upon completing each stage of the blood sampling, freeze-drying and storage of the cells in the vial has maintained a careful continuation of a process code (bar code or other identifying meta-data that tracks the order and the baby's identity). The code is attached to the vial and the combined vial and coding information are deposited in a standardized delivery envelope, which standard is created according to a preferred embodiment. In this case the delivery envelope can be mailed by U.S. Postal Service to a centralized processing facility where further information about the particular account can be affixed and/or made integral to the vial and the vial is then posted by U.S. Postal Service to the address destination requested by the requester.

In alternative embodiments of the invention the processing materials can include an address label so that the technician's mailing of a completed stored sample can be made directly to the requesting parent. Additionally, the delivery can be by courier service or mailing service that provides careful tracking of the delivery for greater security.

Example 2

An alternative embodiment of the invention provides further for desiccating (lyopreserving) the stem cells while incorporating the lyoprotectant trehalose into the cord blood stem cells, enabling the stem cells to be dried to less than 3 grams per gram water and still maintain viability following rehydration. This method can follow the procedures of S. A. Meyers, ["Dry storage of sperm: applications in primates and domestic animals"; 2006; Reprod Fertil Dev. 2006; 18 (1-2): 1-5], herein incorporated by reference in its entirety.

Figure 2B:
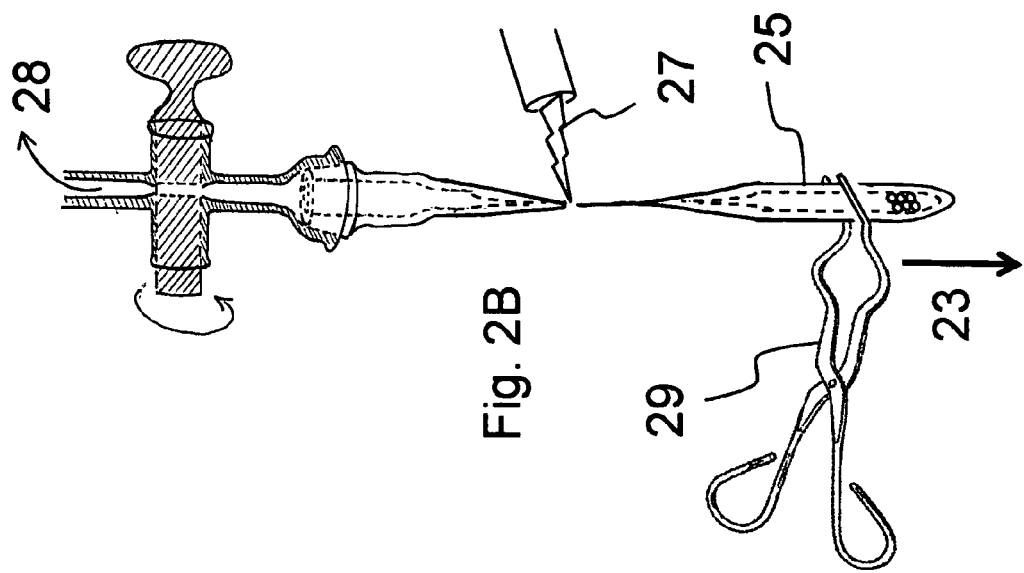
FIG. 2B illustrates a flame-off step to create a sealed, glass ampule having a specialized gaseous environment within.
Figure 2A:
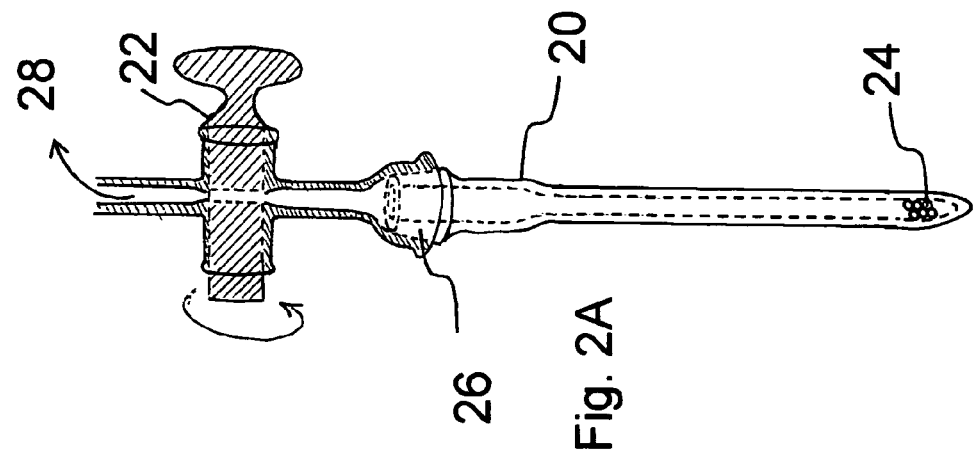
FIG. 2A illustrates a glass flame-off pipette containing stem cells according to an embodiment.
Figure 3:
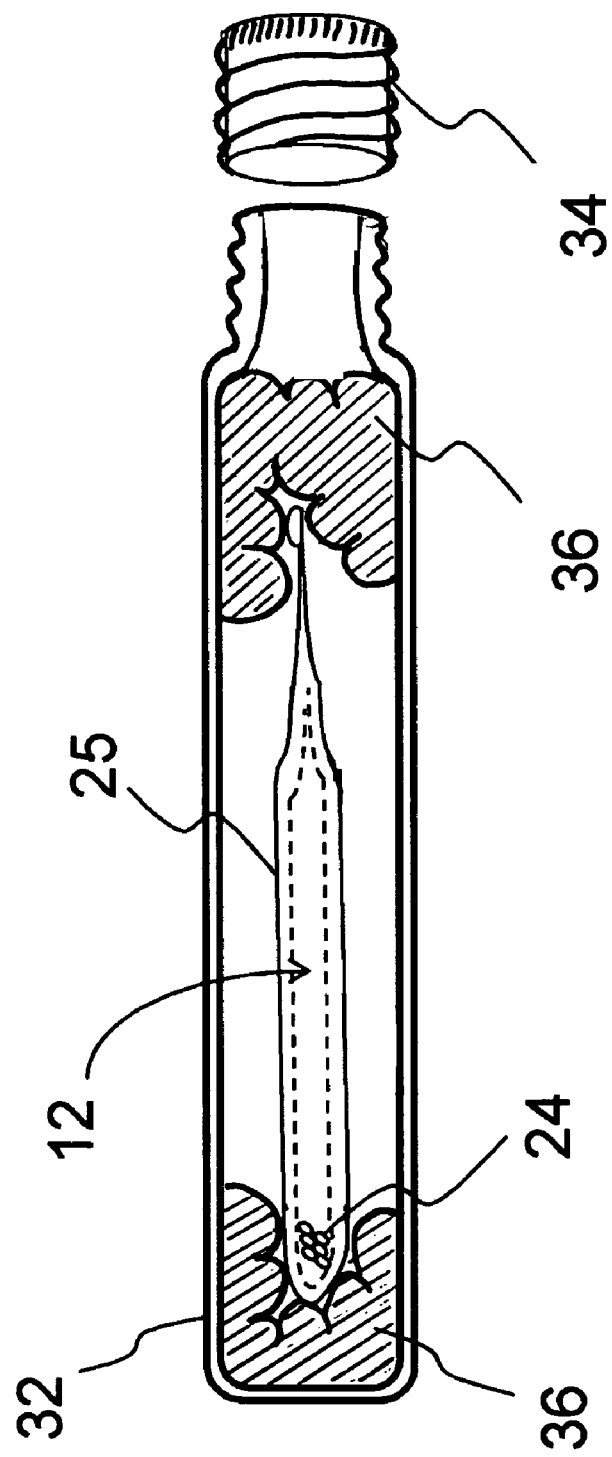
FIG. 3 illustrates a two-layer storage container according to an embodiment, wherein an airtight, permanently sealed ampule is located within an outer storage cylinder.

Embodiments of the invention can be further illustrated with reference to the Figures. Referring to FIG. 1, a container 25, which can be, for example, a plastic, glass or metal ampule or vial, contains preserved stem cells 24, immediately surrounded by a specialized environment 12, which environment can be, without limitation, a vacuum, a nitrogen gas, a gas mixture low in oxygen or devoid of oxygen, or a denser medium, such as a non-reactive plastic, or a preservative gel or other preserving medium. An ampule with a relative vacuum or low oxygen environment can be created as in FIG. 2A, wherein a glass flame-off pipette 22 containing stem cells 24, is located adjacent a stopcock 22 in a glass vacuum rack, with the glass pipette 22 being sealably connected by a greased, ground-glass stopper/flange 26. A vacuum 28 can be exerted (by a vacuum pump or cryotrap) through a conduit in the stopcock 22 to pull air and/or oxygen out of the pipette 22. Referring to FIG. 2B, the flame-off step is accomplished while a vacuum is being exerted (or a non-oxygen environment maintained), with the pipette held by tongs 29 as a torch flame 27 heats the pipette above the stored stem cells and then the melted portion of the pipette is stretched in a downward direction 23 to pull the melting glass closed at a narrow waist region. At this narrow waist point, after melting the tube closed, the glass can rapidly cool after removal of the flame 27 and the glass waist easily snapped to form ampule 25. A two-layer storage container according to an embodiment is illustrated in FIG. 3, wherein an airtight, permanently sealed ampule 25 containing stem cells 24 in the presence of a vacuum or nitrogen environment (or inert gas, or protective medium) 12 is located with an outer storage cylinder 32 having a screw cap 34, and with cotton wadding 36 further protecting the ampule 25.

FIG. 4 illustrates a succession of web pages or web screens that can appear according to an embodiment as part of the business method of providing an offer to a potential customer and the recording of order information and completion of the ordering transaction, wherein: a first business offering web page 40 can present to the customer a choice of obtaining a description of services and/or a hyperlink to begin an order; a subsequent web page 42 can include data-entry (or text-entry) windows 45, which can include pull-down data selection windows (or menus of participating professionals, hospitals and clinics), for the customer to enter identifying and transaction information, such as but not limited to customer name and address, physician, hospital or clinic and/or expected birth date (or estimated sampling procedure date); a further secondary screen 44 containing level of service choices 47 (e.g., an inexpensive customer option can include simplest sampling/extraction/storage method, information storage and simple ampule sent to customer, whereas a more expensive option may include an expensive ampule, expensive sampling method, more elaborate and/or complete storage information and record, dual storage in safe-deposit box with a partner bank and in an ampule sent to the customer) a further secondary screen 46 providing cost, invoice and/or payment information (for example, without limitation, an initial order fee, a specimen preparation fee, a storage container fee, shipping fees and, if the SSP Company is providing custodial storage, an annual storage fee); a further screen 48 providing legal terms, which screen can include an interactive button to register customer's agreement to the legal terms (such as, without limitation, providing notice to the child at age of majority); and, inter alia, a further page 50 that can include an interactive button 43 to cause the order to be generated, and/or to initiate the processing of the submitted order.

FIG. 5 illustrates business steps according to another embodiment, wherein: at step 52 a customer places an order; at step 53 the order information is received and/or registered and/or recorded; at step 54 the order information is matched against a database listing 55; at step 56 a service order is generated, which can be an automated step; at step 57 a service order memo is created in email and or printed (in which fields are automatically filled in from the order information and/or the database information extracted in correspondence to the order information. The memo can read as follows, or in similar fashion:

"Dear <<SERVICE PROVIDER>> Please carry out standard procedure <<STORAGE I>> for customer <<XYZ>>. Attached are procedure protocols, specimen mailers and payment details. Sincerely, <<SSP Company>>"

At step 58 the medical procedure is specified from a rule-based software engine that links the customer information and desired location for the procedure to appropriate and available protocols that are stored and indexed in the SSP Company database (which can include specific protocols for the blood and/or tissue sampling, stem cell extraction, cell freeze-drying, preservation and ampule storage), a mailer specification and label are generated, and payment to the service provider is detailed and scheduled; and step 59 is transmission of the completed service order to the medical professional. Steps 57, 58 and 59 can be automated.

Figure 6:
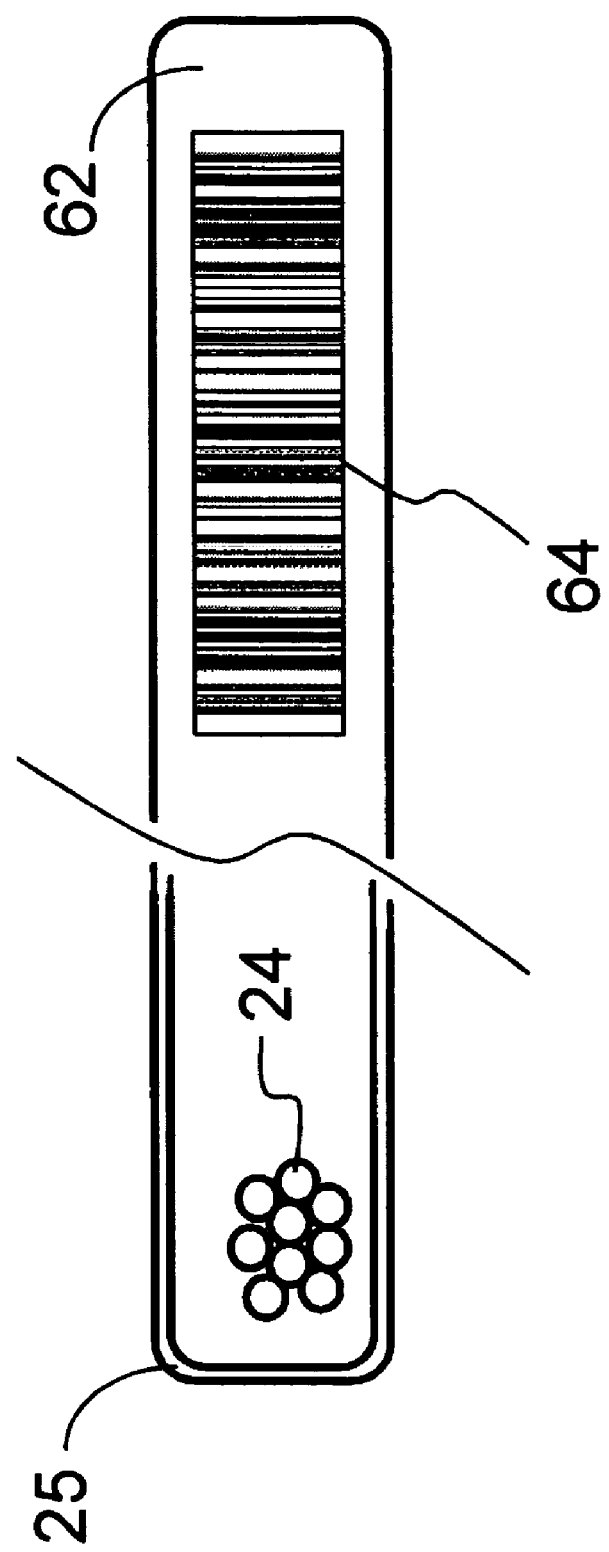
FIG. 6 illustrates a storage ampule upon which is permanently affixed a data component, according to an embodiment.

FIG. 6 illustrates a storage ampule 25 containing stem cells 24 having a covering layer 62 upon which is permanently affixed a data component 64, which data component 64 can be, for example, without limitation, bar code, optical storage, microfiche or other information record.

Example 3

A further embodiment provides another example, illustrated by reference to FIG. 7, of a sequence of business steps according to the invention. FIG. 7 generally shows a flow chart describing a Web-based ordering process that is connected to automated generation of service-order that direct the steps of performing medical service steps, packaging and delivering storage containers to a storage site or to a customer; and/or delivering to the customer physical or digital keys to access the storage site, and/or code-release keys to initiate physical delivery of the stored vial to the customer. In more detail, the following steps are illustrated in FIG. 7. At step 720, a customer accesses a web site that offers the storage service or storable stem-cell product. At step 730, the customer orders services on the web site, such as, for example, providing medical professional and hospital/clinic information, providing dates, choosing level of service, entering data or meta-data to be included later in (or on) the storage container. This information can include names, dates, parents' DNA data, parents' medical history, inter alia, as well as information that may be subsequently and automatically pulled from other $3^{rd}$ party databases through the Internet in response to information entered by the customer. At step 740, the customer pre-pays for extraction and storage (such as, for example, paying by credit card, or paying by pass-through billing to an obstetrician and/or through hospital and/or clinic fees). At step 750, the customer agrees to a binding contract (including, without limitation, a legal electronic signature, a waiver concerning liability, and/or the customer expressly assuming risk and liability on behalf of the minor child). At step 760, the SSP company server connects the customer's order information to a SSP company database or to one or more $3^{rd}$ party databases to obtain additional data or information to be used in generating a service order and/or used in subsequent formation and delivery of the storage method and service, such as, without limitation, information about procedures, locations, practitioners, hospitals, clinics, regulations, materials, storage facilities, banks, costs, risks, re-infusion, probabilities, service delivery, postal delivery, scientific data, storage containers and other information related to the customer-provided information and/or related to information needed for the service order. Typically, this data will be pulled from the SSP company and $3^{rd}$ party databases by software program routines that automatically generate the service order; some of this information can be independent of the information provided by the customer's order entry, while other information can be dependent upon the customer's order entries. At step 770, the company software automatically generates a service order to participating professionals, hospitals, clinics and/or other service providers. At step 780, the SSP company software transmits electronically the Service Orders and portion of prepayment to practitioners, hospitals and clinics (optionally including a preaddressed postal or courier mailer envelope that can be subsequently used by the medical professional(s) to send the sampled and stored stem cells directly to a chosen storage facility or to the customer). At step 790, the medical and preservation services are performed by the professional practitioners in the hospital or clinic (for example, without limitation the umbilical cord is sectioned, blood extracted, stem cells extracted, stem cells preserved, stem cells stored in a storage container, and the container labeled with data and/or code tracking information). At step 800, data is entered by medical professionals, converted and/or transferred automatically onto the data component that is to be stored with the stored stem cells (such as, for example, information about the child/patient, the birth event, the sampling, extraction and preservation procedures. At step 810 the data component is merged with the storage container, such as by an automated labeling procedure. At step 820, the storage container is packaged in a mailer, which can be a mailer that has been preaddressed to the customer or to a centralized storage facility (such as described at step 780 above). At step 830, the mailer is sent/delivered to the customer, such as by U.S. postal service or by a courier service, and/or, at step 840, the package can be sent to a centralized storage facility or to a $3^{rd}$ party storage location, such as a safety-deposit box in a bank. At step 850, a code or key can be sent to the customer allowing later recovery from the storage facility or safety deposit box (where the code can be a digital password that allows the customer to signal a storage facility to automatically ship the stored sample to the customer or to another $3^{rd}$ party).

Figure 8:
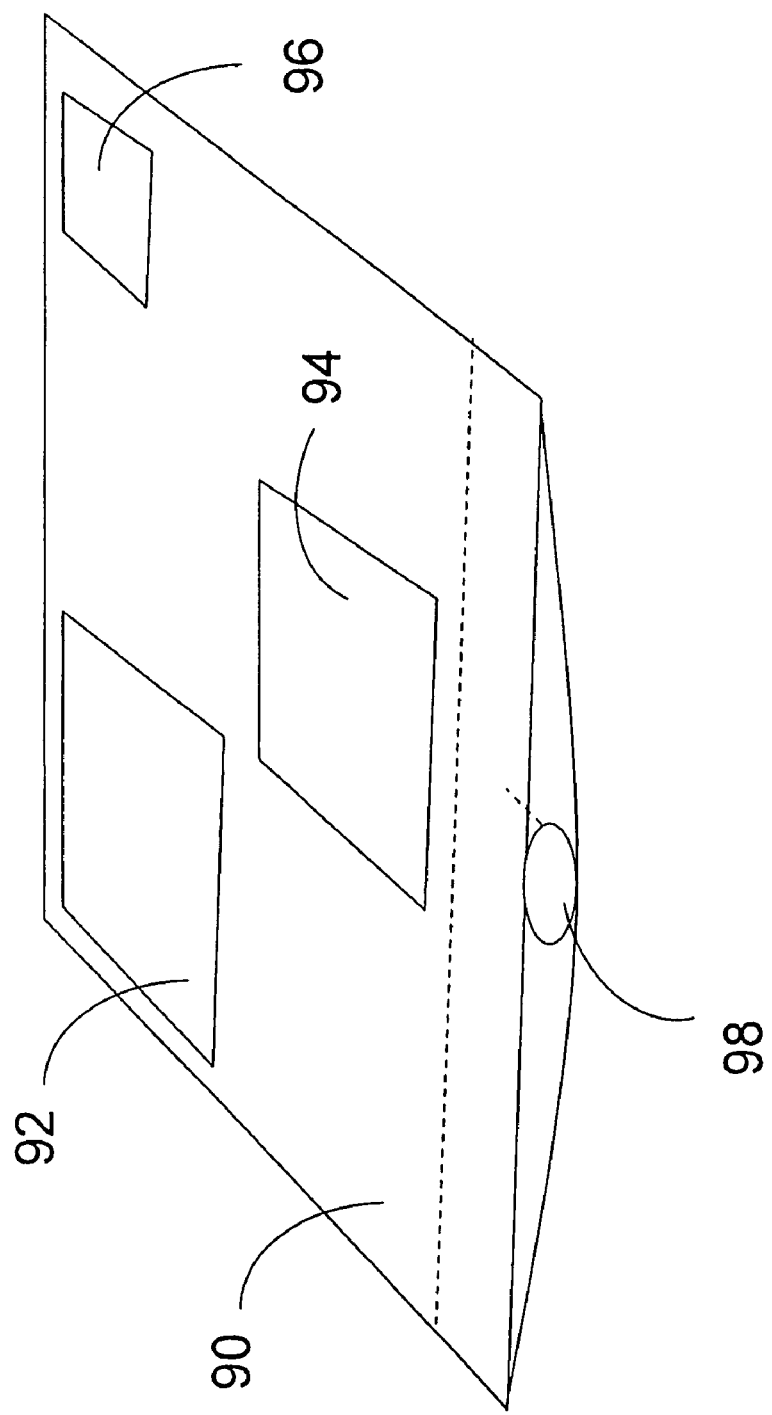
FIG. 8 illustrates a specialized transmittal envelope according to an embodiment of the invention.

FIG. 8 shows a transmittal envelope 90 that is especially suited and/or designed for a particular storage container 98 and for routing by addressing 94 to a particular storage facility, whereby the transmittal envelopes bear prepaid postage 96 and sufficient identifying coding 92 so that the envelopes can be automatically manipulated by robotic handling, including being processed, stored and later retrieved and reshipped to an end-user customer based on the information in the exterior coding 92. In the storage facility, automated storage methods can include providing sorting, processing, aligning and storage placement machinery wherein the specialized envelopes are stored efficiently and compactly in storage carousels and/or other automated containers that allow machine access, deposit and retrieval and automated reshipment based on the storage facility receiving a password-protected, storage-release directive from an end-user customer.

While the present invention has been described in conjunction with preferred embodiment, one of ordinary skill, after reading the foregoing specification, will be able to effect various changes, substitutions of equivalents, and other alterations to the compositions and methods set forth herein. It is therefore intended that the patent protection granted hereon be limited only by the appended claims and equivalents thereof.

What is claimed is:

1. A computer-based and Internet-based service-business transaction system for generating a service order and selling services, comprising:
   a computer system and an application server connected to a relational database;
   an input means configured to enable a customer to input information to the relational database relative to the customer;
   a communication means configured to enable communication of information about service-provider professionals, service-provider facilities or both service-provider professionals and service-provider facilities to potential customers of the business-transaction system and communication of information about one or more customers' choosing of services of the service-provider professionals, service-provider facilities or both service-provider professionals and service-provider facilities to the business-transaction system;
   a planning means;

a front office purchasing interface configured to provide purchase order information and marketing information and to receive at least one order from at least one customer; and a processor configured for processing orders received from the front office purchasing interface, wherein the database is configured to store service-order information about each of a plurality of service providers and contains at least one of a service-method and service-provider information, said service-provider information comprising at least one of a service-method, service-provider data and pre-service processing methods, the system has a services entry interface and means for services entry authorization and customer authorization, the application server hosts business system software and is accessible to customers via the Internet, the database, the front office purchasing interface, the planning means, and the processor are interoperably connected, the computer system is configured such that a customer accessing the application server through an Internet connection causes the business system software to initiate the planning means based on input information from the customer, the planning means connects or relates the customer's input information to information about the services and retrieves from the database information sufficient to complete and deliver a standard service order, and wherein the at least one of a service-method and service-provider information contained in the database is a service-method corresponding to a service that is at least one of a medical service, a biomedical service, a research service, and a biomedical research service, and wherein the at least one of a service-method and service-provider information contained in the database is at least one of a biomedical service-method, biomedical research service-method, and biomedical service-provider information and are related to at least one of biological materials and biomedical materials processing method, and wherein the planning means is configured to enable a customer accessing the system to plan a medical or biomedical research service.

2. The computer-implemented, online, business-transaction system of claim 1, further comprising the computer system includes computer program instructions to provide:

(a) a first user interface configured to accept, from a first user, an identification of one of a plurality of service providers and information identifying at least one service provider who is to be authorized to provide at least one service relative to at least one customer, wherein the computer program instructions are further capable of providing a first user access to a web site, determining if the first user is authorized to enter information into the database, and further configured to enable a first user to enter into the database information identifying a service provider who is to be authorized to provide a service (b) a second user interface configured to accept user credentials and an identification of one of the plurality of service providers, wherein the second user interface is accessible by a customer who is not the first user or one of the plurality of service providers, wherein the second user interface is further configured to determine if the customer is authorized to generate a service-order, relative to the one of the plurality of service providers, wherein the business transaction system is further configured such that, when a customer is accessing the database, a. the system determines if the user credentials accepted from the customer by the second user interface correspond to information requirements criteria stored in the database in association with the one of the plurality of service providers; and b. if the customer is authorized, the system generates a service order relating to the one of the plurality of service providers and provide the generated service order to the service provider.

3. The system of claim 1, wherein the service-provider professionals, service-provider facilities or both service-provider professionals and service-provider facilities about which the communication means is configured to enable communication of information about comprise medical or biomedical research professionals, hospitals, clinics or a combination thereof, and the services chosen by customers about which the communication means is configured to enable communication of information about comprise services of medical or biomedical research professionals, hospitals, clinics or combination thereof to the business transaction system, or both.

4. The system of claim 1, wherein the database further stores information about at least a plurality of medical service professionals, hospitals, clinics or a combination thereof who deliver at least one of the services of delivering babies, attending births, taking samples of umbilical cord tissue or blood, storing umbilical cord tissue or blood, extracting cord blood stem cells, and storing cord blood stem cells.

5. The system of claim 1, wherein the planning means is configured to enable a customer accessing the system to plan a medical or biomedical research service relating to stem-cell storage.

6. The system of claim 1, wherein the database contains at least one service-method corresponding to a service that is at least one of a medical service, a biomedical service and a biomedical research service and further the service is at least one of a biological material sampling service, biological material processing service, biological material storage service, biological sample storage service, biological sample processing service, biological tissue sample-taking service, human umbilical-cord-blood sample-taking service, human tissue processing service, stem-cell extraction service, stem-cell processing service, and stem-cell storage service.

7. A computer-based and Internet-based method of facilitating a transaction online between a customer and a third-party service provider, wherein said method is performed by a single facilitator company, the method comprising the steps of:

providing an online computer-based business-transaction system communicably coupled to a database;

storing service-order information relating to a plurality of services and service providers in the database, wherein at least service-providers can access the database via a first interface and enter information into the database and at least one customer can access the website and/or database via a second interface;

displaying on a web site offered services from the database;

providing an offer online to sell at least one service, this step further comprising providing an online presentation or menu of at least one of medical, biomedical, medical research and biomedical research services selectable by a customer, said services selectable being performable by at least one medical, biomedical, medical research and biomedical research service provider, and presenting at least one of an Internet-based customer sign-up procedure or purchase form and an Internet-based ordering process or ordering page;

detecting an order on a computer from a customer for the at least one service;

generating a service order automatically by a computing means; and outputting the automatically generated service-order from a computer wherein the step of generating a service-order further comprises the step of automatically generating a service-order that directs at least one of the steps of (i) performing at least one of medical service steps, biomedical service steps, medical research service steps and biomedical research service steps, (ii) packaging and delivering service-product containers for containing at least one of a biological material, samples and data to a service-provider site, an intermediary service-provider site or to the customer; and (iii) delivering to the customer at least one of physical or digital keys to access the service-provider site or intermediary service provider site, and code-release keys to initiate delivery of the service-product to the customer, wherein the service product is at least one of a biological material, a sample and data (wherein the data are related to the service or the service-product).

8. The method of claim 7, wherein the one or more service providers is or are at least one of a medical or biomedical research doctor, a medical or biomedical research technician, a medical or biomedical research clinic and a medical or biomedical research hospital.

9. The method of claim 7, wherein the step of providing an offer online to sell at least one service further comprises providing an offer online to sell at least one of a collection, testing and processing service.

10. The method of claim 7, wherein the step of providing an offer online to sell at least one service and further comprising providing an online presentation or menu of at least one of medical, biomedical, medical research and biomedical research services selectable by a customer, said services performable by at least one medical, biomedical, medical research and biomedical research service provider, further comprises the step of providing on a web site a selectable menu of a plurality of biomedical research services each having functional objectives, the services selectable by a customer, said services performable by at least one biomedical research service provider.

11. The method of claim 7, wherein the step of providing an offer online to sell at least one service and further comprising providing an online presentation or menu of at least one of medical, biomedical, medical research and biomedical research services selectable by a customer, said services performable by at least one medical, biomedical, medical research and biomedical research service provider, further comprises the steps of:

providing on a web site a selectable menu of a plurality of biomedical functional objectives, each biomedical functional objective corresponding to a biomedical service performable by a biomedical service-provider in the facilitator company database, detecting an order online for one or more biomedical functional objectives, matching in the relational database the one or more biomedical functional objectives to a service-provider providing a biomedical service corresponding to the ordered functional objective, generating a service order for the corresponding biomedical service and outputting the service order from a computer and delivering the outputted service order to the service provider.

12. The method of claim 7, wherein the menu is a pull-down menu.

13. The method of claim 7, wherein the step of storing service-order information about each of a plurality of service providers in the database further comprises the step of authorizing at least one service provider to access the web site and enter information into the database.

14. The method of claim 13, wherein the step authorizing at least one service provider to access the web site and enter information into the database further comprises the steps of (i) enabling via computer program instructions in the computer system authorized entry of service-provider information to the facilitator company database by a first user via a web site, by performing the following steps:

accepting via a first user interface, from the first user, an identification of one of a plurality of service providers, providing the first user access to a web site of the facilitator company, and determining if the first user is authorized to enter information into the database; and (ii) receiving from at least one first user into the database information identifying at least one service provider who is to be authorized to provide at least one service.

15. The method of claim 7, wherein the step of providing an offer online to sell at least one service further comprises authorizing a customer via the facilitator company web site by performing the following steps:

accepting via a second user interface user credentials and an identification of one of a plurality of service providers, wherein the second user interface is accessible by a customer who is not the first user or one of the plurality of service providers, determining if the customer is authorized to generate a service-order, relative to the one of the plurality of service providers.

16. The method of 15, wherein authorizing a customer via the facilitator company web site further comprises accessing the database to determine if the user credentials accepted from the customer by the second user interface correspond to information requirements criteria stored in the database in association with the one of the plurality of service providers.

17. The method of claim 16, further comprising the additional steps of accessing the database to determine if the user credentials accepted from the customer by the second user interface correspond to information requirements criteria stored in the database in association with the one of the plurality of service providers; and, if the customer is authorized, then generating a service order relating to the one of the plurality of service providers and providing the generated service order to the service provider.

18. The method of claim 7, further comprising selling a service to a customer via a succession of web pages or web screens.

19. The method of claim 7, wherein the step of detecting an order on a computer from a customer for the at least one service further comprises the steps of:

providing at least one Web-based ordering page;
recording of order information, and
registering the customer order.

20. The method of claim 19, wherein the step of providing at least one Web-based ordering page further comprises
providing the customer access to a first business-offering web page that presents to the customer a choice of at least one of obtaining a description of services and operating a hyperlink to begin an order.

21. The method of claim 19, wherein the step of providing at least one Web-based ordering page further comprises
providing the customer access to a further secondary screen containing levels of service choices,
providing the customer access to a subsequent web page comprising data-entry or text-entry windows for the customer to enter identifying and transaction information, wherein the identifying and transaction information includes at least one of customer name and address, service facility, and expected or estimated service date,
displaying to the customer a planning interface, wherein the planning interface is configured to enable a customer utilizing the planning interface to access a presentation of available options for services in order to facilitate a transaction for at least one of a plurality of service products, and
wherein the step of displaying to the customer a planning interface further comprises providing customer access to one or more web screens providing at least one of cost information, invoice information, legal information, and payment information.

22. The method of claim 21, wherein cost information comprises at least one of information about an initial order fee, a specimen preparation fee, a storage container fee, a shipping fee, and an annual storage fee.

23. The method of claim 21, wherein the planning interface is configured to enable a customer utilizing the planning interface to establish a service plan.

24. The method of 21, wherein the data-entry or text-entry windows include pull-down data selection windows or menus of at least two participating service professionals and service facilities.

25. The method of claim 19, wherein the step of providing at least one Web-based ordering page further comprises providing legal terms.

26. The method of claim 19, wherein the step of providing at least one Web-based ordering page further comprises providing legal terms and an interactive button to register customer's agreement to the legal terms.

27. The method of claim 19, wherein the step of providing at least one Web-based ordering page further comprises providing legal terms and establishing a service contract for a customer.

28. The method of claim 19, wherein the step of providing at least one Web-based ordering page further comprises providing legal terms and establishing a service contract for a customer, wherein customer agrees to a binding contract that includes at least one of a legal electronic signature, the customer expressly assuming risk, and a waiver concerning liability.

29. The method of claim 19, wherein the step of recording of order information further comprises at least one of the steps of
(a) receiving the customer's order for services on the web site by way of receiving information entered by the customer via a web page as to at least one of service professional or service facility information, dates, choice of level of service, and data or meta-data to be included later in the performance of the service or processing of the service-product; and
(b) accessing information automatically from other 3rd party databases through the Internet in response to information entered by the customer.

30. The method of claim 19, wherein the step of D(b) recording of order information further comprises collecting a fee, preferably a prepaid fee, from the customer to effect the service.

31. The method of claim 30, wherein the customer pays in advance for the service, fully electronically via the web, preferably using a bank credit card.

32. The method of claim 19, wherein the step of registering the customer order further comprises providing the customer access to a web page that has an interactive button that enables the customer to cause at least one of the order to be generated and the processing of the submitted order to be initiated.

33. The method of claim 7, wherein the step of generating a service-order further comprises the step of
notifying the service provider of the order for the at least one service, thereby facilitating the transaction.

34. The method of claim 33, wherein the step of notifying the service provider of the order for the at least one service, further comprises the step of
at least one of creating an email and printing a service order memo to the service-provider in which email or memo fields are automatically filled in from the order information and database information extracted in correspondence to the order information,
wherein data are obtained from the facilitator company and third-party databases by software program routines that automatically generate the service order.

35. The method of claim 33, wherein the step of notifying the service provider of the order for the at least one service, further comprises the step of
the facilitator company software transmitting electronically one or more service orders and portion of prepayment to service providers, and
optionally, including a preaddressed postal or courier mailer envelope.

36. The method of claim 35, wherein the step of notifying the service provider of the order for the at least one service, further comprises the steps of
the facilitator company software paying a service company a predetermined fee in support of services performed by said company on behalf of said customer, and
accounting for said fee from at least one of said customers.

37. The method of claim 7, wherein the step of generating a service-order further comprises the steps of
a software module run by the facilitator company automatically generating a service order for the service procedure based on a customer's online order, and
forwarding the automated service-order to the service professionals responsible for effecting the service.

38. The method of claim 7, wherein the step of generating a service-order further comprises the steps of
connecting automatically the web-ordering page to a secondary, automated service-order directive transmission, and
providing a web-page presented service, whereby the service provided arranges directly with the service professional to provide the desired service procedure according to the service details selected.

39. The method of claim 7, wherein the step of generating a service-order further comprises the steps of directing a secondary order page to the service technicians employed by the service-provider company or by a 3rd party company, wherein the secondary order page so directed transmits a service requestor's authenticated authorization information, which preferably includes identity information that can be verified by the service provider, and provides specific technical instructions to at least one of the service provider, the service facility and the service technicians.

40. The method of claim 7, wherein the step of generating a service-order further comprises the steps of receiving order data from a customer having entered information into a web-based order form, directing a secondary order page to the service technicians with the order data being moved to a server and then a secondary order being placed by the facilitator company based on the information in the order form, with a forwarded order sheet being delivered by the Internet to participating service providers.

41. The method of claim 7, wherein the step of generating a service-order further comprises the automated steps of matching the order information against a database, specifying a service procedure from a rule-based software engine that links the customer information and desired location for the procedure to appropriate and available protocols that are stored and indexed in the facilitator company database, the facilitator company server connecting the customer's order information to the facilitator company database or to one or more third-party databases to obtain additional data or information to be used in at least one of (i) generating a service order and (ii) in subsequent formation and delivery of the service method and service.

42. The method of claim 41, wherein the additional data or information to be used in generating a service order, used in subsequent formation and delivery of the service method and service, or both used in so generating and in formatting and delivering, further comprises information about procedures, locations, practitioners, hospitals, clinics, regulations, materials, storage facilities, banks, costs, risks, re-infusion, probabilities, service delivery, postal delivery, scientific data, storage containers and other information related to the customer-provided information and/or related to information needed for the service order.

43. The method of claim 7, wherein the biological material is at least one of stem cells, umbilical cord blood, placental blood, DNA, peripheral blood and bone marrow.

44. The method of claim 7, wherein the step of generating a service-order further comprises at least one of detailing payment to the service provider and scheduling payment to the service provider.

45. The method of claim 7, wherein the steps of at least one of detecting an order on a computer from the customer for the at least one service and generating a service order utilize encryption to keep information confidential.

46. The method of claim 7, wherein the step of generating a service-order further comprises the step packaging and delivering service-product containers for containing data to a service-provider site or an intermediary service-provider site, and further comprising the step of the intermediary service-provider site receiving data from the service provider and further processing the data and conveying the further processed data to the customer, wherein the data are related to the service or the service-product.

47. The method of claim 7, further comprising the steps of providing an intermediary service step whereby an intermediate service team receives one or more samples from a first service facility and this team performs subsequent service steps and delivers a service result to the customer.

48. The method of claim 47, further comprising wherein the service result is transforming a sample.

49. The method of claim 48, wherein the sample is cord blood and the step of transforming comprises at least one of extracting stem cells from the cord blood and freeze-drying the extracted stem cells to create a freeze-dried specimen.

50. The method of claim 7, wherein the step of generating a service-order further comprises generating a mailer specification and label.

51. The method of claim 50, wherein the generated service order directs the service provider to at least one of convert and transfer automatically data into a data component.

52. The method of claim 51, wherein the generated service order further directs the data component to be further processed in an intermediate step by at least one of a second $3^{rd}$-party service provider and the first service provider company and returned to the customer as part of delivery of the services.

53. The method of claim 52, wherein the first service provider company is the facilitator company.

54. The method of claim 52, wherein the facilitator company is also a service-provider or an intermediary service provider.

55. The method of claim 7, wherein the step of generating a service-order further comprises the service order directing service technicians maintain data as the service progresses.

56. The method of claim 7, wherein the step of generating a service-order further comprises the service-order directing service technicians to maintain data as the service progresses, the service-product includes data and subsequent intermediate processing of the service-product includes subsequent processing of the service-product data.

57. The method of claim 56, wherein the service-product data comprises DNA data, dates or information that may be pulled from other third-party databases through the Internet.

58. The method of claim 7, wherein the step of generating a service-order further comprises the facilitator company connecting the service-order to a facilitator company database or to one or more $3^{rd}$-party databases in order to obtain additional data or information to be at least one of (i) used in generating a service order and (ii) used in subsequent formation and delivery of the service method and service.

59. The method of claim 58, wherein the additional data or information comprises information about the service delivery, scientific data, procedures, locations, regulations, materials, service facilities, costs, risks, probabilities, and other information related to information needed for the service order.

60. The method of claim 58, wherein some of the additional data or information comprises information that is independent of the information provided by the customer's order entries.

61. The method of claim 7, comprising the additional step of providing a transmittal envelope, a special envelope, or special mailing container, said envelopes or container designed to enclose a service-product container and to carry descriptive, coded information on the exterior of the envelope, which envelope can be transmitted by a postal service or by private courier.

62. The method of claim 61, wherein the envelopes or mailing container assist in the business process of delivering of at least one of the sample, service-result, service-product, service-related data and service-product-related data between the customer and a service facility, wherein the envelopes or mailing container are preaddressed and coded, and wherein the envelope is automatically labeled and addressed as part of the step of generating the service order.

63. The method of claim 62, wherein the envelope or container conveying service-product to the customer with data undergoes further processing at an intermediary service-provider step.

64. The method of claim 61, wherein the envelope or container bears sufficient identifying coding so that the envelopes or container can be automatically manipulated or processed by robotic handling, processed, stored and later retrieved and reshipped based on the information in the exterior coding.

65. The method of claim 64, wherein the envelope or container can be automatically stored in storage carousels managed by automatic handling equipment or robotics.

66. The method of claim 61, wherein the envelope or container bears prepaid postage.

67. The method of claim 7, wherein the step of generating a service-order further comprises the service-order directs a sample is at least one of collected, extracted, preserved, contained, and sealed, and the sealed sample packaged and posted directly from the service facility, or by the primary attending service professionals, and delivered to a subsequent service facility or to the customer.

68. A computer-based and Internet-based method of facilitating a transaction online between a customer and a third-party service provider, wherein said method is performed by a single facilitator company, the method comprising the steps of:
providing an online computer-based business-transaction system communicably coupled to a database;
storing service-order information relating to a plurality of services and service providers in the database, wherein at least service-providers can access the database via a first interface and enter information into the database and at least one customer can access the website and/or database via a second interface;
displaying on a web site offered services from the database;
providing an offer online to sell at least one service, this step further comprising providing an online presentation or menu of at least one of medical, biomedical, medical research and biomedical research services selectable by a customer, said services selectable being performable by at least one medical, biomedical, medical research and biomedical research service provider, and presenting at least one of an Internet-based customer sign-up procedure or purchase form and an Internet-based ordering process or ordering page;
detecting an order on a computer from a customer for the at least one service;
generating a service order automatically by a computing means, wherein this step of generating a service-order directs the performing of medical and biomedical services comprising the steps of
extracting a sample of tissue,
extracting stem cells,
freeze-drying the stem cells, and
delivering freeze-dried stem cells to a customer; and
outputting the automatically generated service-order from a computer.

69. The method of claim 68, wherein the step of generating a service-order directs the performing of medical and biomedical services comprising the further steps of
pipetting the freeze-dried stem cells into a flame-off tube,
reducing the oxygen level in the tube to below that of ambient air,
flaming-off the tube to create an airtight sealed tube,
packaging the airtight sealed tube inside a secondary storage container,
packaging the secondary storage container inside a transmittal envelope and
delivering the transmittal envelope to a customer.

70. The method of claim 68, wherein the container is a vial, coded information is attached to the vial and the combined vial and coded information are deposited in a standardized delivery or transmittal envelope.

* * * * *